United States Patent

Van Hoye

[11] Patent Number: 4,621,193
[45] Date of Patent: Nov. 4, 1986

[54] FLUORESCENT PENETRANT CRACK DETECTION

[76] Inventor: Michael Van Hoye, 5564 Vista del Rio, Anaheim, Calif. 92807

[21] Appl. No.: 673,587

[22] Filed: Nov. 21, 1984

[51] Int. Cl.[4] ............................................. G07N 21/91
[52] U.S. Cl. .................................. 250/302; 250/459.1; 250/461.1; 252/301.19
[58] Field of Search ............... 250/461.1, 459.1, 458.1, 250/302; 252/301.19

[56] References Cited

U.S. PATENT DOCUMENTS

| | | | |
|---|---|---|---|
| 3,415,112 | 12/1968 | Alburger | 73/104 |
| 3,829,690 | 8/1974 | Snyder | 250/302 |
| 3,875,108 | 4/1975 | Koch et al. | 524/141 |
| 3,915,885 | 10/1975 | Molina | 252/301.19 |
| 3,915,886 | 10/1975 | Molina | 252/301.19 |
| 3,965,350 | 6/1976 | Molina | 250/302 |
| 3,992,319 | 11/1976 | Alburger | 252/408.1 |
| 4,249,072 | 2/1981 | Buros | 235/491 |
| 4,273,671 | 6/1981 | Allinikov | 252/301.19 |
| 4,392,982 | 7/1983 | Molina | 252/408.1 |

Primary Examiner—Janice A. Howell
Assistant Examiner—Constantine Hannaher
Attorney, Agent, or Firm—William L. Chapin

[57] ABSTRACT

A method for detecting surface defects in parts by entrapped fluorescent dye penetrant uses a novel applicator which conveys liquid fluorescent dye penetrant by capillary action from a reservoir within the applicator to the surface of the object being tested. The liquid fluorescent dye penetrant has low viscosity and high penetrating power which make the method and applicator effective in detecting minute surface flaws.

4 Claims, 3 Drawing Figures

U.S. Patent  Nov. 4, 1986  4,621,193
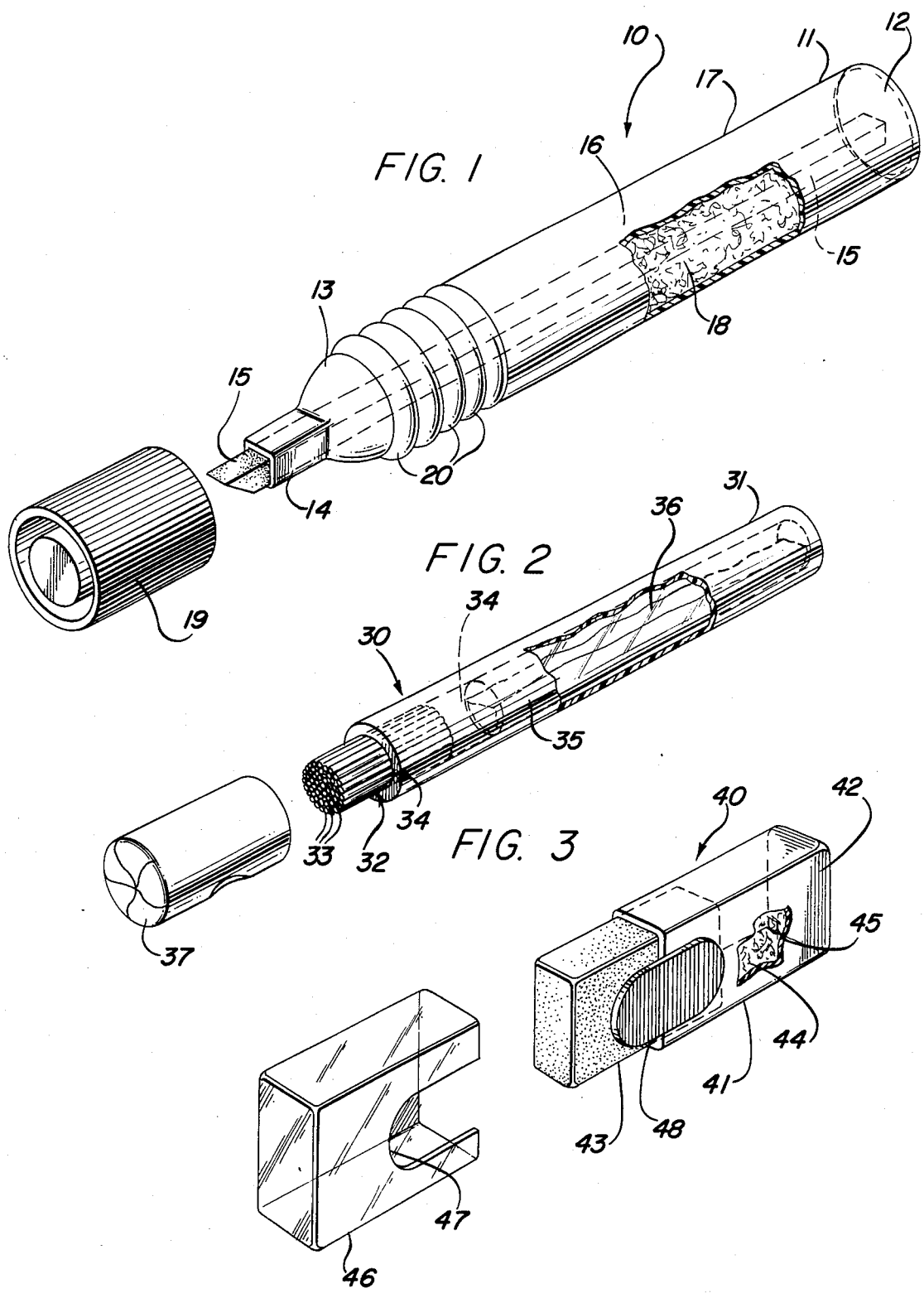

FLUORESCENT PENETRANT CRACK DETECTION

BACKGROUND OF THE INVENTION

1. Field of the Invention

This invention relates to a process, apparatus and materials for use in the detection of surface defects in manufactured parts. More particularly, the invention relates to defect detection methods which employ fluorescent dye penetrants to indicate the presence of defects in a part being tested.

2. Description of Background Art

The use of dye penetrants to detect small flaws in critical manufactured components such as jet engine turbine blades is well known. Typically, flaw detection by the dye penetrant method requires the following sequence of steps.

First, the object to be tested is cleaned thoroughly, using a vapor degreaser, for example. Next the object is immersed in a dye penetrant solution which contains a solvent and a dye, typically one which fluoresces brightly when irradiated by long-wave ultraviolet radiation, in the approximate range of 3000 Å (300 nm) to 4000 Å (400 nm). Alternatively, dye penetrant may be sprayed upon the surface of the object to be tested. Third, excess dye penetrant solution is removed from the surface of the part with the aid of another solution, an emulsifier. The part is then washed and dried. Finally, the part under test is illuminated with a source of long-wave ultraviolet radiation. Dye penetrant which has been entrapped in samll voids such as cracks, seams or porous areas fluoresces brightly when illuminated by the ultraviolet radiation source, providing a visual indication of small defects which would otherwise escape visual detection. Sometimes a developer solution is applied to the surface of the part after that surface has been cleansed of excess dye penetrant solution. The function of the developer solution is to draw up to the surface of the part, by capillary action, dye which has been entrapped in voids some distance below the surface. This makes the dye and therefore the void more readily visible.

Fluorescent dye penetrant solutions commonly used are either water soluble, or oily, non-water soluble. The latter type penetrant solution requires a hydrocarbon solvent such as mineral spirits to remove excess penetrant solution from the surface of the object to be tested. Alternatively, an emulsifier may be applied to the part being tested, rendering the excess oily penetrant solution soluble in water, which may then be used to cleanse the surface of the part.

The dye penetrant inspection processes just described are generally effective in performing their intended function of detecting small surface flaws in manufactured parts. However, existing dye penetrant testing processes all have certain drawbacks which limit their usefulness for "in-process" inspection applications. For example, the immersion method of applying dye penetrant to a part to be tested often requires that the part be pre-heated, and that the part remain immersed for a substantial period. Thus the immersion method of penetrant testing can be time consuming. Also, large and cumbersome parts require large immersion tanks and large volumes of dye penetrant solution.

Existing oily penetrants have a characteristic high mobility which causes ultra-small penetrant entrapments to migrate and thin out to the point where their visibility is greatly reduced. Furthermore, oily penetrants are incompatible with soldering fluxes and therefore cannot be conveniently used for the inspection of defective solder joints. On the other hand, various delicate electronic components cannot tolerate water contact. Therefore, circuit boards containing these components cannot be tested using water-soluble penetrant solutions.

The spray method of applying dye penetrant also has limitations The volatile components used in the spray often present fire and health hazards. Also, uncontrollable overspray can present a problem. The present invention overcomes some of the problems inherent in the existing methods of dye penetrant flaw detection.

OBJECTS OF THE INVENTION

An object of the present invention is to provide an "in-process" fluorescent dye penetrant inspection process which may be used to quickly detect surface discontinuities in manufactured parts.

Another object of the invention is to provide a fluorescent dye penetrant detection process which employs an applicator apparatus which is readily portable.

Another object of the invention is to provide a fluorescent dye penetrant which has low viscosity and high penetrating power, facilitating the rapid transport of penetrant to voids in the article being tested.

Various other objects and advantages of the present invention, and its most novel features, will become apparent to those skilled in the art by reading the accompanying specification and claims.

It is to be understood that although the invention disclosed herein is fully capable of achieving the objects and providing the advantages described, the characteristics of the invention described herein are merely illustrative of the preferred embodiments. Accordingly, I do not intend the scope of my exclusive rights and privileges in the invention to be limited to the details of the embodiments described. I do intend that reasonable equivalents, adaptations and modifications of the various embodiments and alternate forms of the present invention which are described herein be included within the scope of this invention as defined by the appended claims.

SUMMARY OF THE INVENTION

Briefly stated, the present invention comprehends a novel process for applying fluorescent dye penetrant to manufactured parts for the purpose of detecting surface imperfections or flaws in those parts. The basic embodiment of the apparatus employed in the process comprises an applicator similar in appearance and function to a conventional felt tip pen. A novel formulation of fluorescent dye penetrant contained within the applicator has a lower viscosity and greater penetrating power than existing penetrants. This permits penetrant to be applied in an effective manner to surfaces to be checked merely by drawing the tip of the applicator over the area to be inspected.

BRIEF DESCRIPTION OF THE DRAWINGS

FIG. 1 is a perspective view of the basic embodiment of the fluorescent penetrant applicator according to the present invention.

FIG. 2 is a perspective view of a second embodiment of the apparatus according to the present invention.

FIG. 3 is a perspective view of a third embodiment of the invention.

DESCRIPTION OF THE EMBODIMENTS

Referring now to FIG. 1, the basic embodiment of an apparatus for applying fluorescent flaw detection penetrant according to the present invention is shown. The largest component of the applicator 10 is a cylindrical tube 11 made of thin gauge metal or plastic. One end of cylindrical tube 11 is sealed by a transversely disposed circular disc 12 bonded circumferentially to the cylindrical wall of cylindrical tube 11. At the opposite end of cylindrical tube 11, a transition section 13 having the shape of a frustrum of a cone joins the cylindrical body to a smaller diameter, hollow cylindrical tip 14. The base of the cone is congruent with the cylindrical wall of cylindrical tube 11, and the apex of the cone is truncated by coaxial cylindrical tip 14.

An elongated wicking member or nib 15 made of felt or similar relatively stiff, absorbent material extends axially outward through hollow cylindrical tip 14. Nib 15 has a generally rectangular, uniform cross section, and an end surface cut at a dihedral angle to the longitudinal axis of the nib.

Nib 15 also extends inward through hollow cylindrical tip 14 and transition section 13 into the cylindrical cavity 16 comprising the interior region of hollow cylindrical tube 11. The cross-sectional size of nib 15 is sufficiently larger than the cross-sectional size of the aperture in hollow cylindrical tip 14 to produce an interference fit between the inner wall of tip 14 and the outer surfaces of nib 15. Thus after nib 15 has been inserted into tip 14 during the manufacture of applicator 10, the nib is retained securely within the tip.

Cylindrical cavity 16 within tube 11 is adapted to holding liquid fluorescent penetrant 17 and thus functions as a reservoir for the penetrant. Preferably, a quantity of absorbent material 18 such as cotton partially fills cavity 16. Absorbent material 18 retains penetrant in interstices between solid material. Liquid penetrant 17 is conducted out through nib 15 to the tip of the nib from cavity 16 by capillary action.

A generally cylindrical shaped end cap 19 is adapted to fitting tightly over nib 15 and transition section 13 when the applicator is not in use. This prevents evaporation of penetrant 17.

As shown in FIG. 1, the forward end of the outer cylindrical wall of cylindrical tube 11 back of transition section 13 may be provided with a plurality of coaxial annular grooves 20, regularly spaced along the longitudinal axis of cylindrical tube 11. Grooves 20 permit the forward end of cylindrical tube 11 to bend readily in a radial direction. Thus when nib 15 is pressed with sufficient force down at an angle on a work surface, the end of cylindrical tube 11 is caused to flex. This minimizes the small radius flexures of nib 15 which could otherwise occur, substantially increasing the life of nib 15.

Fluorescent dye penetrant 17 contained in cavity 16 has the following novel formulation:

| | |
|---|---|
| Ethoxylated Alkyphenol | 10% approx. |
| Diphenyl Alkyl Phosphate | 10% approx. |
| Petroleum Hydrocarbons | 75% approx. |
| Fluorescent dye from the group comprising fluoranthrene and Napthalmide | 5% approx. |

The novel formulation of fluorescent dye penetrant disclosed above has lower viscosity and greater penetrating power than existing penetrants To use the apparatus of FIG. 1 to detect cracks, porosity and other surface imperfections in such manufactured parts as jet turbine blades, the area of the surface to be inspected is first swabbed with a cleaner such as denatured alcohol. The surface is then wiped dry with a clean cloth. For surfaces which are extremely dirty, this cleaning and drying step may be repeated if necessary.

After the surface to be checked has been cleaned, the end cap 19 is removed from applicator 10, and felt nib 15 is drawn across the surface until the surface is well covered with fluorescent dye penetrant. The penetrant is allowed to remain on the surface for approximately 15 seconds. Additional passes of the applicator nib over the surface may be made as required for locating extremely fine surface discontinuities.

After fluorescent dye penetrant has been applied to the surface as described, the surface is cleaned of excess penetrant by spraying or swabbing the surface with a cleaner such as denatured alcohol, and the surface is dried by wiping it with a clean cloth. A "black light" (long-wave ultraviolet lamp) is then used to illuminate the surface. Voids in the surface of the part are indicated by a bright fluorescence of fluorescent dye penetrant entrapped in the voids.

A second embodiment 30 of a fluorescent dye penetrant applicator according to the present invention is shown in FIG. 2. In the second embodiment, the main body of applicator 30 is a hollow cylindrical tube 31 made from flexible plastic and sealed at one end of the cylinder. Extending longitudinally outward from the opposite end of cylindrical tube 31 is a parallel bundle 32 of fibers 33 made from a synthetic non-absorbing material such as glass. Fiber bundle 32 fits tightly into the open end of cylindrical tube 31, and extends inward some distance into the cylindrical cavity 34 comprising the interior of cylindrical tube 31.

A cylindrical shaped, sealed ampule 35 containing fluorescent dye penetrant 36 lies conformally within cylindrical cavity 34. Ampule 35 is fabricated from thin-wall, easily frangible glass sometimes referred to as "onion skin" glass. Ampule 35 is inserted into cavity 34 during the assembly of applicator 30, before fiber bundle 32 is inserted into the open end of cylindrical tube 31.

An end cap 37 shaped generally like a hollow cylindrical tube open at one end and sealed at the other end with a transverse wall is adopted to fit over the end of cylindrical tube 31. End cap 37 may be made from paper or plastic and is used to protect fiber bundle 32 from becoming contaminated by dust, etc.

To use applicator 30, end cap 37 is removed from cylindrical tube 31. Tube 31 is then bent or squeezed until thin-wall glass ampule 35 breaks, releasing fluorescent dye penetrant 36 into cylindrical cavity 34. The end of tube 31 containing fiber bundle 32 is then tilted downward, moistening the inner ends of fibers 33 with fluorescent dye penetrant 36. Voids between parallel fibers 33 then transmit by capillary action fluorescent dye penetrant to the outer surface of fiber bundle 32. The outer surface of fiber bundle 32 may then be placed in contact with the surface of the object to be tested, and drawn across the surface to apply fluorescent dye penetrant. The sequence of steps performed in the process of using applicator 30 to detect surface defects in parts is exactly the same as has been described for the basic embodiment of the apparatus according to the present invention.

A third embodiment 40 of a fluorescent dye penetrant applicator according to the present invention is shown in FIG. 3. In this embodiment, the main body of applicator 40 is an elongated rectangular cross section hollow tube 41. An integral back wall 42 disposed perpendicularly to the longitudinal axis of tube 41 seals the rear face of the tube. An elongated, rectangular cross section nib 43 made of felt or similar relatively stiff, absorbent material extends longitudinally outward through the front rectangular shaped opening in tube 41. The cross-sectional size of nib 43 is sufficiently larger than the cross-sectional size of the front rectangular shaped opening in tube 41 to produce an interference fit between the inner surfaces of tube 41 and the outer surfaces of nib 43. Thus after nib 43 has been inserted part way into tube 41 during the manufacture of applicator 40, the nib is retained securely within the tube.

With nib 43 inserted part way into tube 41, a box-shaped cavity 44 exists within tube 41, extending longitudinally from the inner surface back wall 42 of tube 41 forward to the back surface of nib 43. Cavity 44 is adapted to holding liquid fluorescent penetrant and thus functions as a reservoir for the penetrant. Preferably, a quantity of absorbent material 45 such as cotton partially fills cavity 44. Absorbent material 45 retains penetrant in interstices between solid material. Liquid penetrant is conducted out through nib 43 to the front surface of the nib by capillary action.

An end cap 46 in the shape of elongated, rectangular cross-section, hollow tube is adopted to fitting over that portion of nib 43 which extends outward from tube 41. An elongated oval shaped notch 47 is cut through one of the wider walls of end cap 46, backwards from a front, open edge of the tube. An elastic oval shaped button 48 is fastened on the facing wider wall of tube 41. Button 48 is adopted to form an interference fit with the inner facing walls of notch 47. Thus when end cap 46 is slid over nib 43 until the front edges of end cap 46 and tube 41 abut, button 48 engages notch 47 in an interference fit, retaining tube 41 and end cap 46 in a locking configuration. The tight interface between the front edges of cap 46 and tube 41 minimizes evaporation of liquid fluorescent cent dye penetrant. Applicator 40 is used to detect surface defects in parts exactly as has been described for the basic embodiment of the apparatus according to the present invention.

What I claim is:

1. A process for detecting surface voids in objects comprising:
   (a) swabbing the surface of the object to be tested with an applicator containing a fluorescent liquid dye penetrant,
   (b) allowing the penetrant to remain on said surface for a period of time sufficient to permit said penetrant to reach the minimum size voids which it is desired to detect,
   (c) cleaning the surface of said object,
   (d) illuminating the surface of said object with ultraviolet light to reveal by fluorescent dye penetrant which is entrapped in said voids, and
   (e) visually inspecting the surface of said object for dye penetrant entrapped in said surface voids.

2. The process of claim 1 wherein said fluorescent dye penetrant applicator comprises:
   (a) a sealed, hollow container having an opening communicating with the interior of said reservoir container, said reservoir container containing a fluorescent liquid dye penetrant, and
   (b) a wikcing member adapted to resiliently contact said surface of said object to be tested extending outward from the interior of said reservoir container, the outer perimetric contact surface of said wicking member with said opening in said container fitting tightly within said opening in said container, said wicking member being made of a material adapted to convey by capillary action fluorescent liquid dye penetrant from the interior of said reservoir container to the exposed outer surface of said wicking member.

3. The process of claim 1 wherein said dye penetrant comprises essentially the follow formulation, stated by weight percentages:

| Ethoxylated Alkylphenol | 10% ± 5% |
| Diphenyl Alkyl Phosphate | 10% ± 4% |
| Petroleum Hydrocarbons | 75% ± 5% |
| Fluorescent Dye | 5% ± 2% |

4. The process of claim 3 wherein said fluorescent dye is further defined as being a fluorescent dye from the group comprising fluoranthrene and napthalmide.

* * * * *